(12) United States Patent
Blake

(10) Patent No.: US 12,251,294 B2
(45) Date of Patent: Mar. 18, 2025

(54) MEDICAL DRESSING COVERING SYSTEM AND METHOD OF USING THE SAME

(71) Applicant: Luke Blake, Terre Haute, IN (US)

(72) Inventor: Luke Blake, Terre Haute, IN (US)

( * ) Notice: Subject to any disclaimer, the term of this patent is extended or adjusted under 35 U.S.C. 154(b) by 926 days.

(21) Appl. No.: 17/210,445

(22) Filed: Mar. 23, 2021

(65) Prior Publication Data

US 2021/0205144 A1 Jul. 8, 2021

Related U.S. Application Data

(63) Continuation-in-part of application No. 16/175,912, filed on Oct. 31, 2018, now Pat. No. 10,953,199, which is a continuation-in-part of application No. 15/802,258, filed on Nov. 2, 2017, now Pat. No. 10,804,890, which is a continuation-in-part of application No. 15/377,146, filed on Dec. 13, 2016, now Pat. No. 10,177,717.

(51) Int. Cl.
*A61F 13/02* (2024.01)
*A61F 13/00* (2006.01)

(52) U.S. Cl.
CPC ...... *A61F 13/0233* (2013.01); *A61F 13/0266* (2013.01); *A61F 2013/00182* (2013.01)

(58) Field of Classification Search
CPC .............. A61F 13/0233; A61F 13/0266; A61F 2013/00182
See application file for complete search history.

(56) References Cited

U.S. PATENT DOCUMENTS

| | | | |
|---|---|---|---|
| 3,916,887 A | 11/1975 | Kelly | |
| 4,324,237 A | 4/1982 | Buttaravoli | |
| 4,485,809 A * | 12/1984 | Dellas | A61L 15/42 602/57 |
| 4,743,232 A * | 5/1988 | Kruger | A61F 13/023 604/304 |
| 4,875,473 A | 10/1989 | Alvarez | |
| 5,086,764 A | 2/1992 | Gilman | |
| 5,344,415 A | 9/1994 | deBusk et al. | |
| 5,395,675 A | 3/1995 | Altholz et al. | |
| 5,707,348 A | 1/1998 | Krogh | |
| 5,860,420 A | 1/1999 | Wiedner et al. | |
| 6,090,076 A | 7/2000 | Lane, Jr. | |

(Continued)

*Primary Examiner* — Deanna K Hall
(74) *Attorney, Agent, or Firm* — Reichel Stohry Dean LLP; Mark C. Reichel; Natalie J. Dean

(57) ABSTRACT

Medical dressing covering system and method of using the same. An exemplary dressing system comprises a primary dressing configured to adhere to a patient and to cover a location on the patient thereby inhibiting said location from being contaminated, said primary dressing defining an outer perimeter edge; a cover dressing having a central section and a peripheral section, said central section of said cover dressing being transparent wherein said primary dressing is visible when viewed through said central section; and a cover adhesive positioned on a lower surface of said peripheral section wherein said lower surface of said peripheral section is configured to adhere to the patient around said outer perimeter edge of said primary dressing whereby said cover dressing extends over and covers said primary dressing such that said cover dressing prevents contamination of said primary dressing.

13 Claims, 15 Drawing Sheets

(56) References Cited

U.S. PATENT DOCUMENTS

| | | | |
|---|---|---|---|
| 6,124,521 A | 9/2000 | Roberts | |
| 6,132,399 A | 10/2000 | Shultz | |
| 6,988,511 B2 | 1/2006 | Tang | |
| 7,612,248 B2 * | 11/2009 | Burton | A61L 15/42 |
| | | | 602/42 |
| 8,029,479 B2 | 10/2011 | Guthrie | |
| 9,668,822 B2 | 6/2017 | Czajka, Jr. et al. | |

* cited by examiner

MEDICAL DRESSING COVERING SYSTEM AND METHOD OF USING THE SAME

PRIORITY

The present application is related to, claims the priority benefit of, and is a continuation-in-part application of, U.S. patent application Ser. No. 16/175,912, filed Oct. 31, 2018 and issued as U.S. Pat. No. 10,953,199 on Mar. 23, 2021, which is related to, claims the priority benefit of, and is a continuation-in-part application of, U.S. patent application Ser. No. 15/802,528, filed Nov. 3, 2017 and issued as U.S. Pat. No. 10,874,471 on Dec. 29, 2020, which is related to, claims the priority benefit of, and is a continuation-in-part application of, U.S. patent application Ser. No. 15/377,146, filed on Dec. 13, 2016 and issued as U.S. Pat. No. 10,177,717 on Nov. 6, 2018. The contents of each of the aforementioned patent applications and patents are hereby incorporated into the present disclosure in their entirety.

BACKGROUND

The disclosure and prior art relates to dressing devices and more particularly pertains to a new dressing device for preventing contamination of a medical site and inadvertent removal of a dressing from the medical site.

BRIEF SUMMARY

An embodiment of the disclosure meets the needs presented above by generally comprising a dressing adhered to a patient covering a catheter. The dressing has a top layer removably covering a base layer. The base layer adheres to the catheter and the patient. The top layer is fluid impermeable. A surgical drape adhesively engages the top layer more strongly than the top layer is engaged to the base layer wherein removal of the surgical drape separates the top layer from the base layer when the surgical drape is removed leaving the base layer uncontaminated and in place covering the catheter after removal of the surgical drape.

The dressing has a top layer removably coupled to a medial layer. A first surface of the medial layer faces away from the top layer. The medial layer is fluid impermeable. A surgical drape adhesively engages the top layer of the dressing when positioned on the patient. The top layer is secured to the surgical drape wherein removal of the surgical drape separates the top layer from the medial layer and the medial layer remains in place coupled to the patient covering the catheter.

An embodiment of the disclosure meets the needs presented above by generally comprising a primary dressing configured to cover a medical site thereby inhibiting the medical site from being contaminated. The primary dressing has an outer perimeter edge. A cover adhesive is positioned on a lower surface of a peripheral section of a cover dressing wherein the lower surface of the peripheral section adheres to the patient around the outer perimeter edge of the primary dressing. A central section of the cover dressing extends over and covers the primary dressing such that the cover dressing prevents contamination of the primary dressing.

The present disclosure includes disclosure of a dressing system, comprising a primary dressing configured to adhere to a patient and to cover a location on the patient thereby inhibiting said location from being contaminated, said primary dressing defining an outer perimeter edge; a cover dressing having a central section and a peripheral section, said central section of said cover dressing being transparent wherein said primary dressing is visible when viewed through said central section; and a cover adhesive positioned on a lower surface of said peripheral section wherein said lower surface of said peripheral section is configured to adhere to the patient around said outer perimeter edge of said primary dressing whereby said cover dressing extends over and covers said primary dressing such that said cover dressing prevents contamination of said primary dressing.

The present disclosure includes disclosure of a dressing system, further comprising a bottom sheet configured to adhere to an adhesive portion of the primary dressing and the cover adhesive of the cover dressing.

The present disclosure includes disclosure of a dressing system, wherein the bottom sheet has an outer portion surrounding an inner portion, and wherein the inner portion is configured for removal from the bottom sheet independent of the outer portion.

The present disclosure includes disclosure of a dressing system, further comprising a tab defined upon the outer portion of the bottom sheet, whereby pulling said tab, after the inner portion has been removed and the dressing system applied to the patient, causes the outer portion to separate from the primary dressing and the cover dressing.

The present disclosure includes disclosure of a dressing system, wherein removal of the inner portion of the dressing system exposes adhesive present upon the primary dressing.

The present disclosure includes disclosure of a dressing system, wherein the primary dressing has an adhesive present upon an entirety of a side of the primary dressing.

The present disclosure includes disclosure of a dressing system, wherein the primary dressing has an adhesive present upon a portion of a side of the primary dressing.

The present disclosure includes disclosure of a dressing system, wherein the primary dressing has an adhesive present upon a side of the primary dressing with at least one internal section of the primary dressing being free of adhesive.

The present disclosure includes disclosure of a dressing system, wherein the at least one internal section of the primary dressing is coated or saturated with a topical antiseptic.

The present disclosure includes disclosure of a dressing system, wherein the primary dressing is sized and shaped to correspond to the size and shape of the central section of the cover dressing.

The present disclosure includes disclosure of a method of using a dressing system, comprising removing the inner portion of the bottom sheet of an exemplary dressing system of the present disclosure to expose adhesive present upon the primary dressing; and positioning the remainder of the dressing system upon a patient at a desired location.

The present disclosure includes disclosure of a method of using a dressing system, further comprising pressing the cover dressing toward the patient to cause the adhesive on the primary dressing to adhere to the patient.

The present disclosure includes disclosure of a method of using a dressing system, further comprising removing the outer portion of the bottom sheet by pulling the tab; and pressing the cover dressing toward the patient again to cause the cover adhesive of the cover dressing to adhere to the patient.

The present disclosure includes disclosure of a method of using a dressing system, further comprising removing the cover dressing so that the primary dressing is fully exposed while being adhered to the patient.

The present disclosure includes disclosure of a method of using a dressing system, further comprising positioning a replacement cover dressing so that it surrounds the primary dressing adhered to the patient; and pressing the replacement cover dressing toward the patient to cause a cover adhesive of the replacement cover dressing to adhere to the patient, surrounding the primary dressing.

The present disclosure includes disclosure of a kit, comprising a dressing system of the present disclosure and at least one additional cover dressing.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein.

Figure 1:
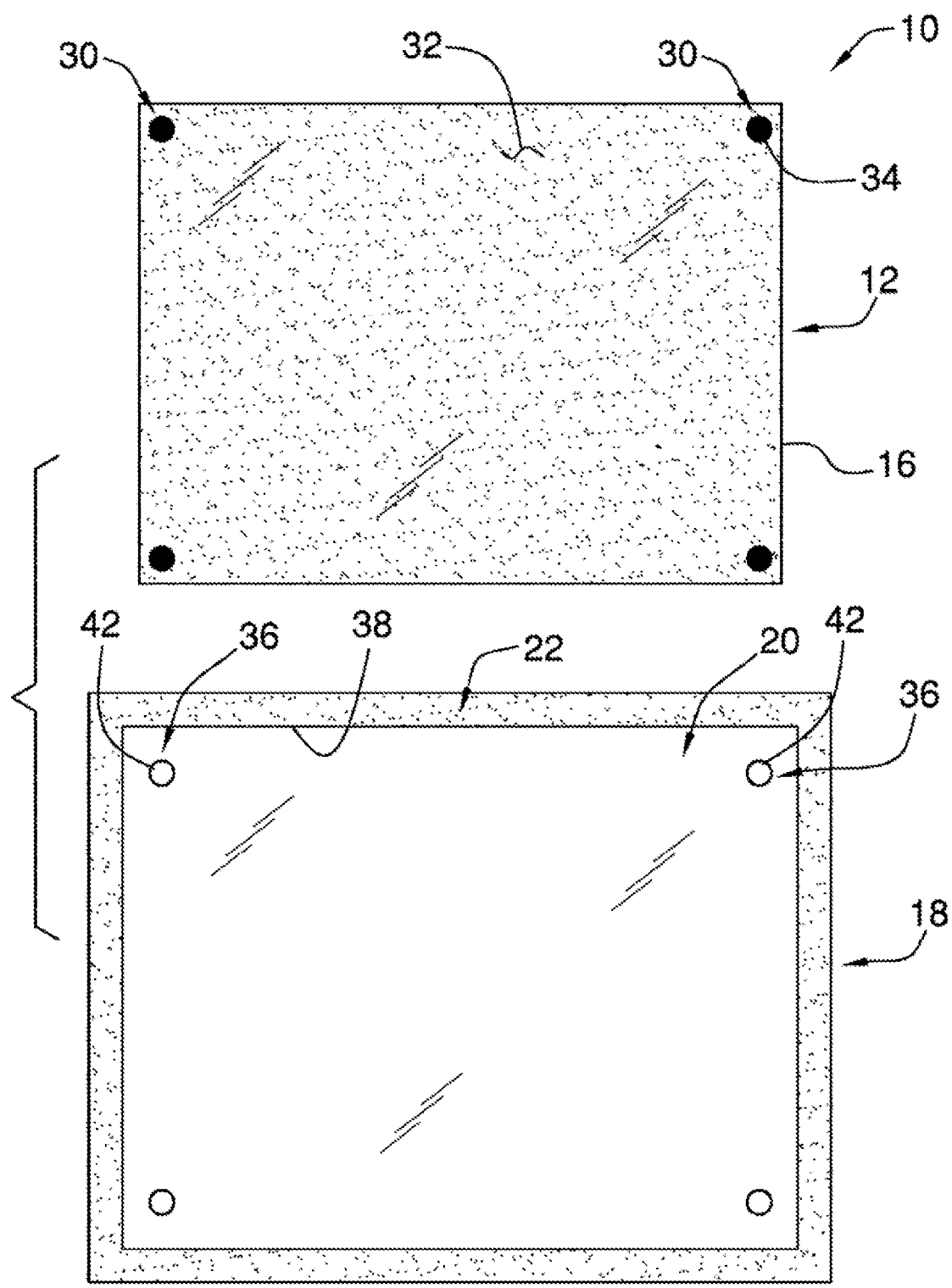
FIG. 1 is a top view of a dual dressing site covering system, according to an exemplary embodiment of the present disclosure.

As such, an overview of the features, functions and/or configurations of the components depicted in the various figures will now be presented. It should be appreciated that not all of the features of the components of the figures are necessarily described and some of these non-discussed features (as well as discussed features) are inherent from the figures themselves. Other non-discussed features may be inherent in component geometry and/or configuration. Furthermore, wherever feasible and convenient, like reference numerals are used in the figures and the description to refer to the same or like parts or steps. The figures are in a simplified form and not to precise scale.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

As best illustrated in FIGS. 1 through 4, the dual dressing medical site covering system 10 generally comprises a primary dressing 12 configured to be adhered to the patient in a conventional manner wherein the surface of the primary dressing to be adhered to the patient is fully covered by adhesive. The primary dressing 12 is configured to cover a medical site 14, such as a catheter site, a wound site, a surgical site, etc., thereby inhibiting the medical site 14 from being contaminated and inhibiting movement of the catheter relative to the patient. The primary dressing 12 has an outer perimeter edge 16. The outer perimeter edge 16 of the primary dressing 12 may be a geometric shape such as a square, rectangle, circle, oval, or the like. A cover dressing 18 has a central section 20 and a peripheral section 22. The central section 20 of the cover dressing 18 is transparent wherein the primary dressing 12 is visible when viewed through the central section 20. The central section 20 has a shape and size substantially equivalent to the primary dressing. This provides for full coverage of the primary dressing 12 by the cover dressing 18 while minimizing bulk.

A cover adhesive 24 is positioned on a lower surface 26 of the peripheral section 22 wherein the lower surface 26 of the peripheral section 22 is configured for adhering to the patient around the outer perimeter edge 16 of the primary dressing 12. Thus, the central section 20 extends over and covers the primary dressing 12 such that the cover dressing 18 prevents contamination of the primary dressing 12. The cover adhesive 24 is positioned on the lower surface 26 of the peripheral section 22 extending completely around the central section 20 wherein the cover dressing 18 is fully occlusive of the primary dressing 12. A lower surface 28 of the central section 20 is free from adhesive wherein the cover dressing 18 is prevented from adhering directly to the primary dressing 12. Thus, the primary dressing 12 is configured to remain in place over the medical site 14 when the cover dressing 18 is removed from the patient. While specifically mentioned as applicable for the medical site 14, it is to be understood the primary dressing 12 may alternatively cover a wound or any other site on the patient where bandaging would be desired. Each of a plurality of base markings 30 is positioned on a top surface 32 of the primary dressing 12. Each of the base markings 30 is positioned proximate to the outer perimeter edge 16 of the primary dressing 12. Each of the base markings 30 is continuously solid within an outermost border 34 of the base marking 30.

Each of a plurality of alignment markings 36 is positioned on the central section 20 of the cover dressing 18. Each of the alignment markings 36 corresponds to an associated one of the base markings 30 such that positioning the alignment markings 36 over the base markings 30 facilitates positioning of an interior edge 38 of the peripheral section 22 proximate to the outer perimeter edge 16 of the primary dressing 12. Placement in this manner defines a gap 40 between the interior edge 38 and the outer perimeter edge 16. The gap 40 has a consistent width extending fully around the primary dressing 12 when each of the alignment markings 36 is properly aligned with the associated one of the base markings 30. Each of the alignment markings 36 is a linear outline 42 complementary to the outermost border 34 of the associated one of the base markings 30. This allows continuity of visual contact with the base marking 30 as the associated alignment marking 36 is positioned over the base marking 30. Further, this arrangement provides for visible confirmation of proper alignment as misalignment will give the appearance of a bulge or offset in the shapes, or a gap between the linear outline 42 and the base marking 30 within the alignment marking 36. A shape of each of the base markings 30 and the alignment markings 36 is shown being circular but could be provided in other shapes.

In use, the cover dressing 18 is fully occlusive and protects the primary dressing 12. The cover dressing 18 can be removed if needed, such as by being contaminated by body fluids during a procedure. The cover dressing 18 is removed leaving the primary dressing 12 intact and uncontaminated. The base markings 30 on the primary dressing 12 facilitate proper positioning of the cover dressing 18. This allows for less bulk, easier application of the cover dressing 18, and helps to insure the gap 40 as desired to prevent the cover dressing 18 from adhesively engaging the primary dressing 12.

With reference now to the drawings, and in particular to FIGS. 5 through 8 thereof, a new medical site dressing device embodying the principles and concepts of an embodiment of the disclosure and generally designated by the reference numeral 110 will be described.

As best illustrated in FIGS. 5 through 8, the catheter dressing system 110 generally comprises a catheter 112 configured to be inserted into a patient in a conventional manner when the patient is undergoing a surgical procedure. A dressing 114 is configured to be adhered to the patient covering the catheter 112 thereby inhibiting the catheter 112 from being contaminated. The dressing 114 has a top layer 116 removably coupled to and covering a base layer 132. The base layer 132 has an adhesive surface 142 facing away from the top layer 116 wherein the base layer 132 is configured for abutting the catheter 112 and the patient wherein the base layer 132 stabilizes a position of the catheter 112 relative to the patient. The top layer 116 is comprised of a fluid impermeable material, of conventional design, such that the top layer 116 inhibits the base layer 132 from being contaminated through the top layer 116. The dressing 114 further comprises a medial layer 118 positioned between the top layer 116 and the base layer 132. The medial layer 118 comprises a first surface 120, a second surface 22 and a perimeter edge 124. The first surface 120 faces away from the top layer 116. The first surface 120 is coupled to the base layer 132 in a conventional manner such as a mild adhesive, static or frictional surfaces, or the like sufficient to hold the dressing 114 together as a coherent single unit until placed on the patient with the base layer 132 covering the catheter 112. The second surface 22 is coupled to the top layer 116 wherein the medial layer 118 couples the top layer 116 to the base layer 132 as described above. Alternatively, if no medial layer 118 is provided, the top layer 116 may be directly coupled to the base layer 132. The medial layer 118 is coupled to the top layer 116 more strongly than to the base layer 132 wherein the medial layer 118 is removed from the base layer 132 with the top layer 116 when the top layer 116 pulled away from the base layer 132.

A peripheral edge 134 of the base layer 132 is inset from the perimeter edge 124 of the medial layer 118 defining an outer portion 138 of the medial layer 118 extending beyond the peripheral edge 134 of the base layer 132 wherein the medial layer 118 completely covers the base layer 132. The perimeter edge 124 of the medial layer 118 is inset from an outermost edge 148 of the top layer 116 wherein the top layer 116 fully covers and extends beyond the perimeter edge 124 of the medial layer 118 to define an outside portion 144 of the top layer 116 extending from the perimeter edge 124 of the medial layer 118. The outside portion 144 of the top layer 116 extends fully around the perimeter edge 124 of the medial layer 118. The top layer 116, the medial layer 118 and the base layer 132 are positioned such that the peripheral edge 134 of the base layer 132, the perimeter edge 124 of the medial layer 118, and the outermost edge 148 of the top layer 116 define a plurality of concentric shapes 150. The first surface 120 between the perimeter edge 124 of the medial layer 118 and the peripheral edge 134 of the base layer 132 is non-adhesive such that the medial layer 118 will not stick to the patient and forms a non-adhesive space around the base layer 132 whereby the top layer 116 is prevented from directly pulling or tugging on the base layer 132 in a direction away from the patient.

A patient adhesive 166, of conventional composition, is positioned on the outside portion 144 of the top layer 116 wherein the top layer 116 is configured for coupling to the patient. The patient adhesive 166 extends fully around the medial layer 118 wherein the top layer 116 is configured to seal to the patient around the medial layer 118 and the base layer 132. A drape adhesive 128 is exposed on the top layer 116 facing away from the base layer 132. A surgical drape 152 is configured to be positioned on the patient in a conventional manner when the patient is undergoing a surgical procedure. The surgical drape 152 adhesively engages the drape adhesive 128 on the top layer 116 of the dressing 114. The top layer 116 is secured to the surgical drape 152 more strongly than to the base layer 132, either directly or through the medial layer 118 if present, wherein removal of the surgical drape 152 separates the top layer 116 from the base layer 132 when the surgical drape 152 is removed from the patient. Thusly, the base layer 132 is configured to be uncontaminated during surgery and remain in place coupled to the patient covering the catheter 112 after removal of the surgical drape 152.

In use, the dressing 114 provides for stabilization of the catheter 112 and protection from contamination while covered by the surgical drape 152 during surgery. Thus, the dressing 114 provides protection to the medical site throughout an entirety of a surgical procedure with automatic removal of the top layer 116 and exposure of the clean base layer 132 upon removal of the surgical drape 152.

Figure 9:
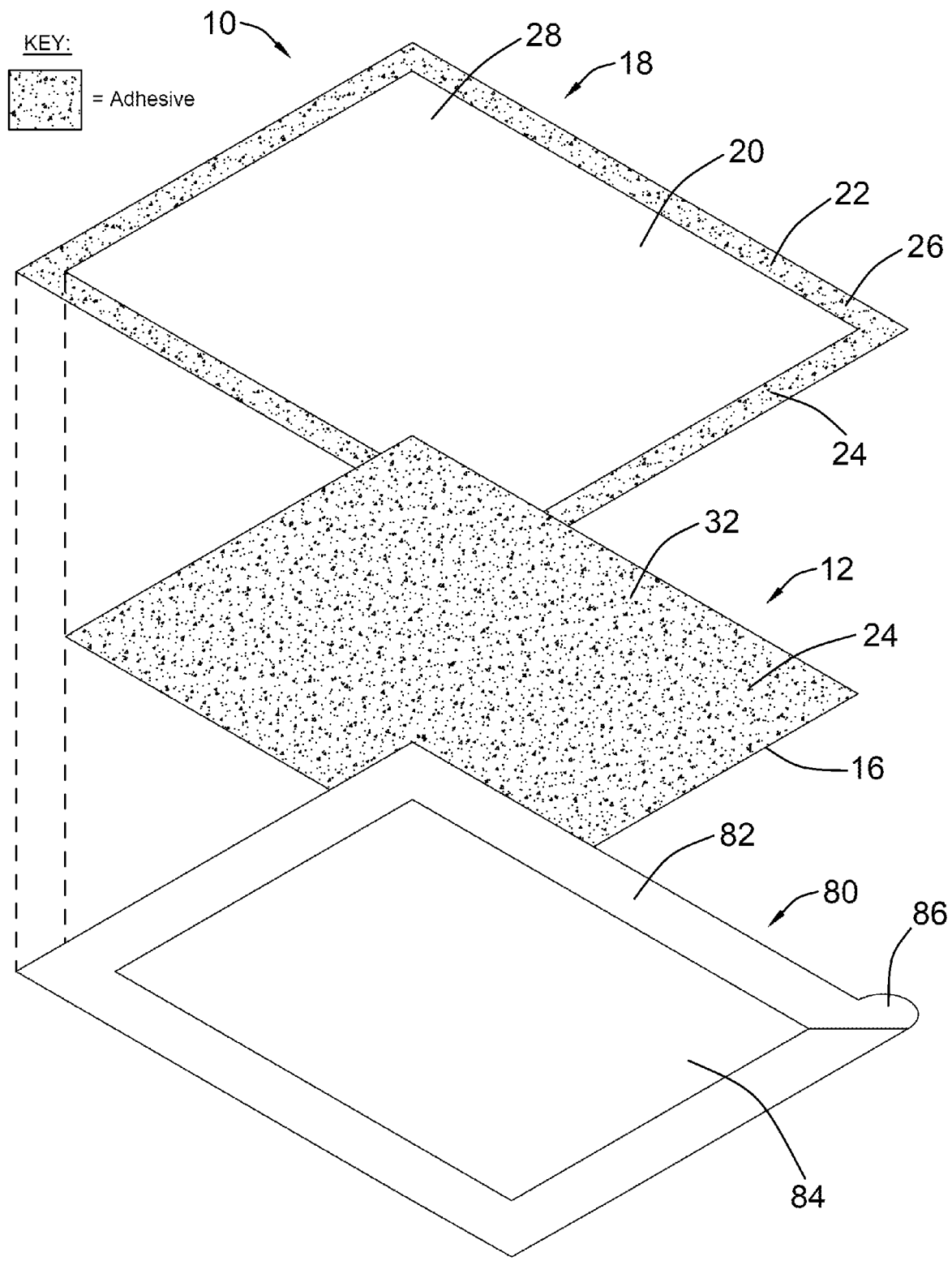
FIG. 9 shows a bottom view of a medical dressing covering system, according to an exemplary embodiment of the present disclosure.
Figure 10:
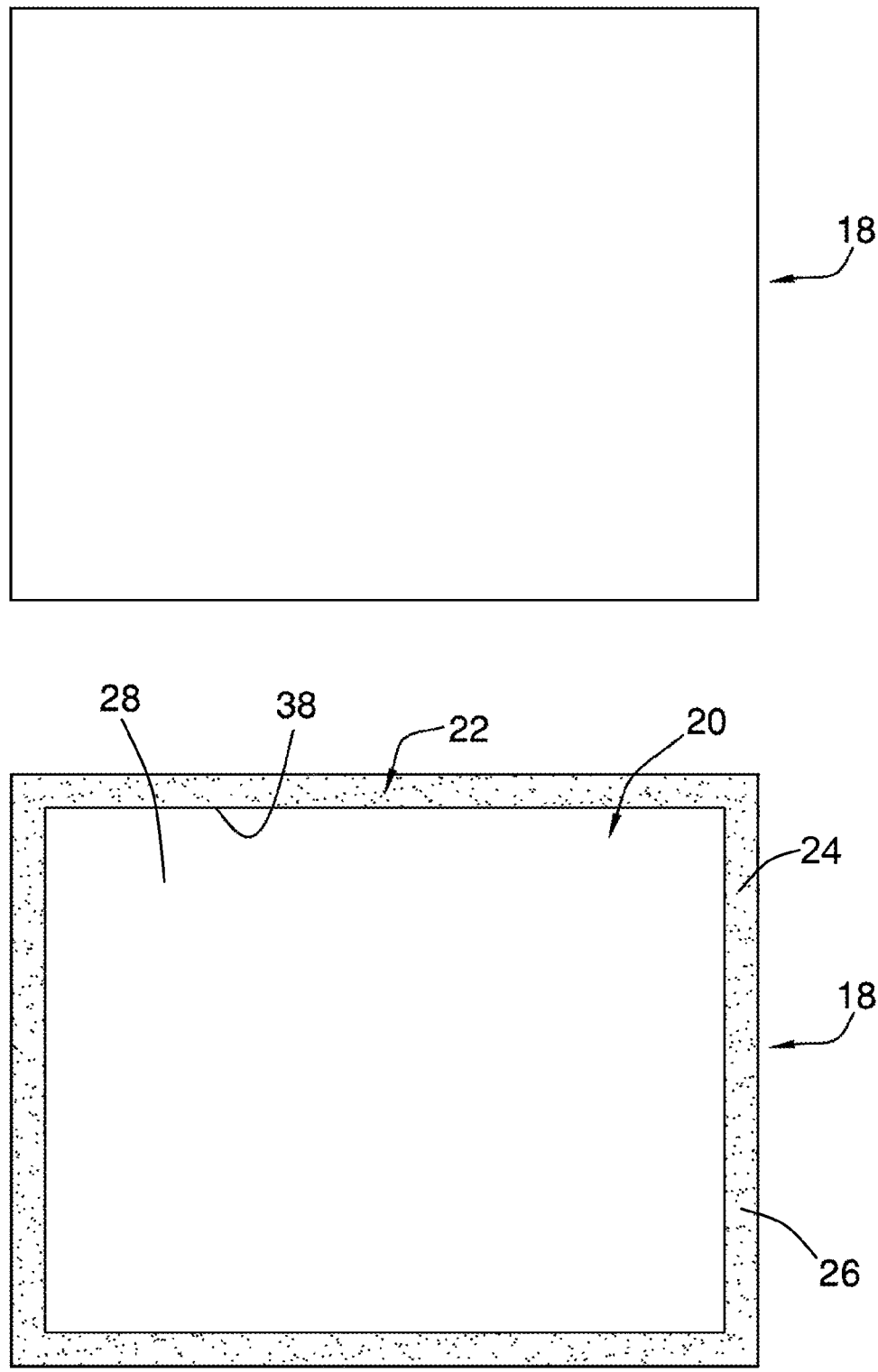
FIG. 10 shows a top view (upper portion of the figure) and a bottom view (lower portion of the figure) of a cover dressing of a medical dressing covering system, according to an exemplary embodiment of the present disclosure.
Figure 11:
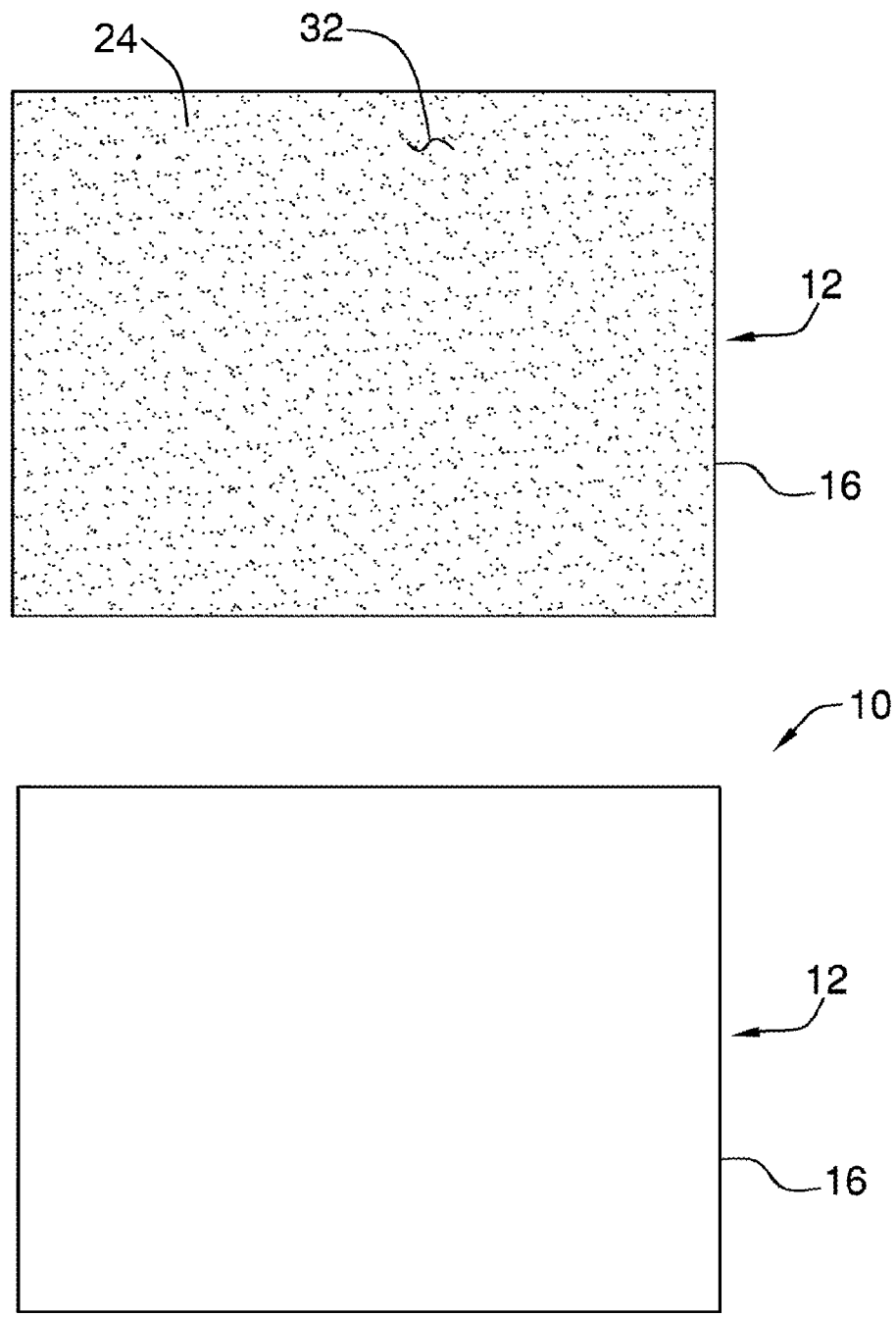
FIG. 11 shows a top view (upper portion of the figure) and a bottom view (lower portion of the figure) of a primary dressing of a medical dressing covering system, according to an exemplary embodiment of the present disclosure.
Figure 12:
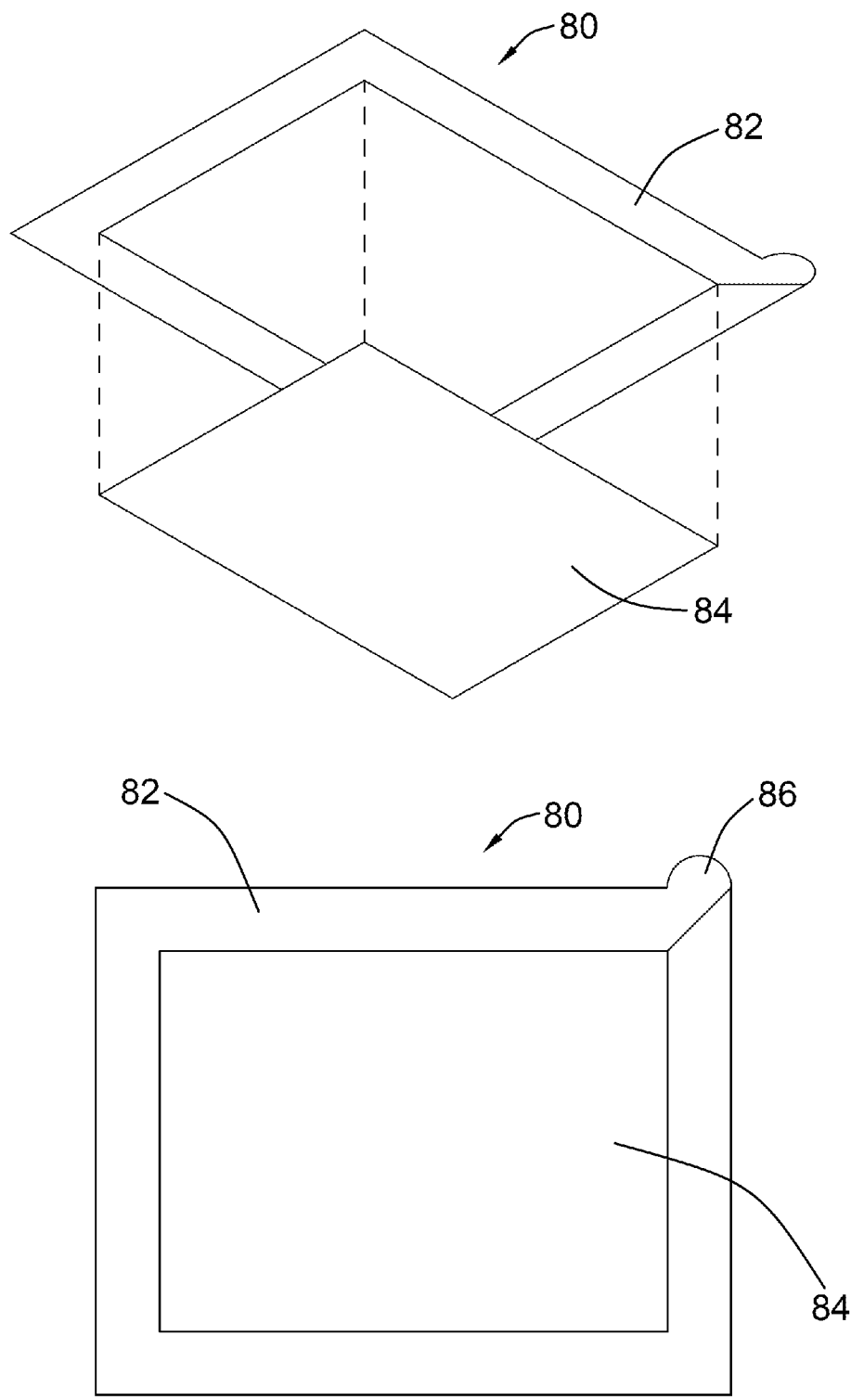
FIG. 12 shows a perspective view of a bottom sheet of a medical dressing covering system, according to an exemplary embodiment of the present disclosure.

An additional embodiment of a covering system 10 of the present disclosure is shown in FIG. 9. As best illustrated in FIG. 9, an exemplary three-layer dressing medical site covering system 10 of the present disclosure generally comprises a primary dressing 12, also as shown in FIG. 11, a cover dressing 18, such as shown in FIGS. 9 and 10 for example, and a bottom sheet 80, such as shown in FIGS. 9 and 12 for example. Such a covering system 10 embodiment can comprise primary dressings 12 and/or cover dressings 18 as otherwise disclosed and described herein, such as those having base markings 30, alignment markings 36, and the like, as may be desired.

Figure 2:
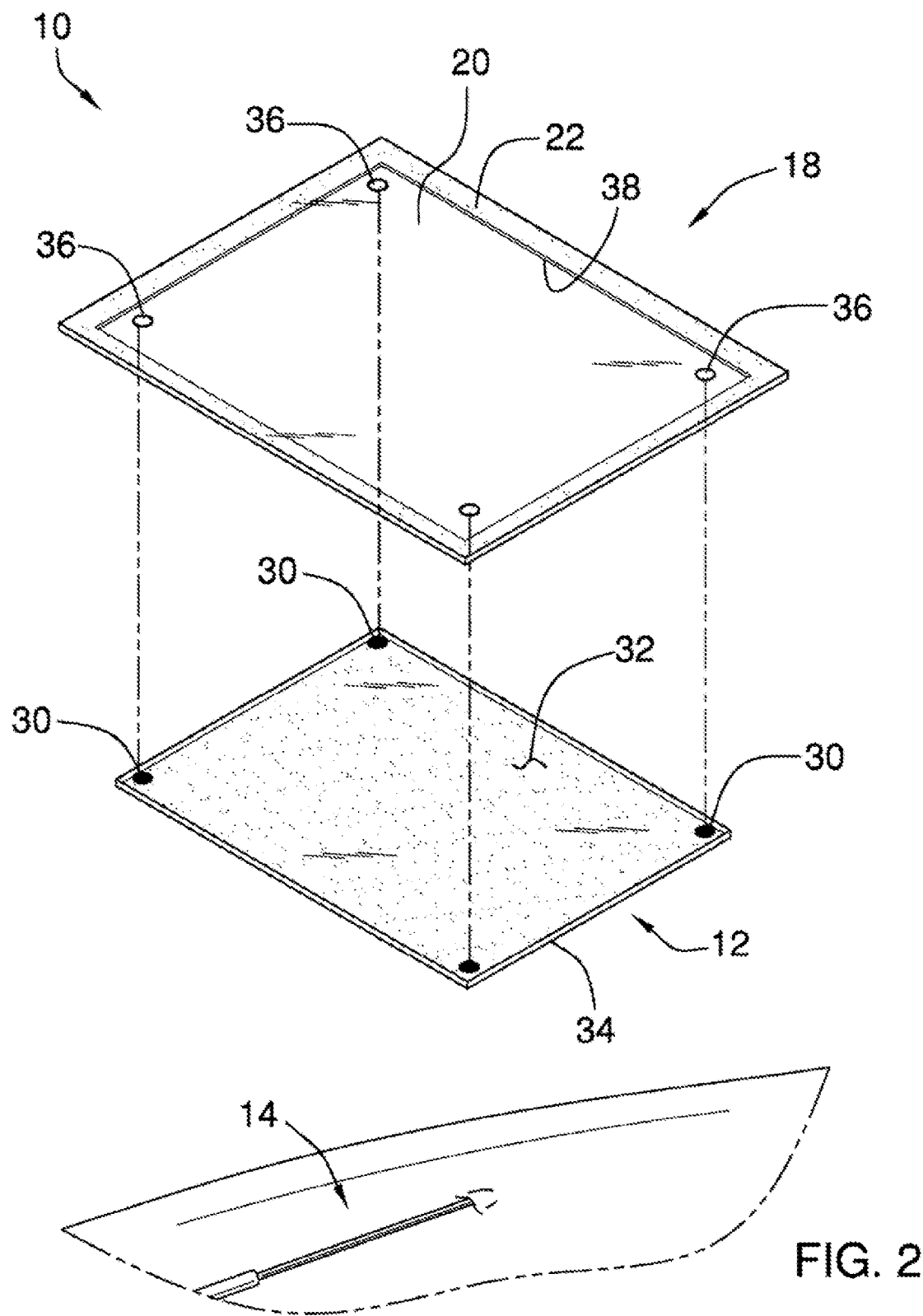
FIG. 2 is an exploded top front side perspective view of a site covering system, according to an exemplary embodiment of the present disclosure.
Figure 3:
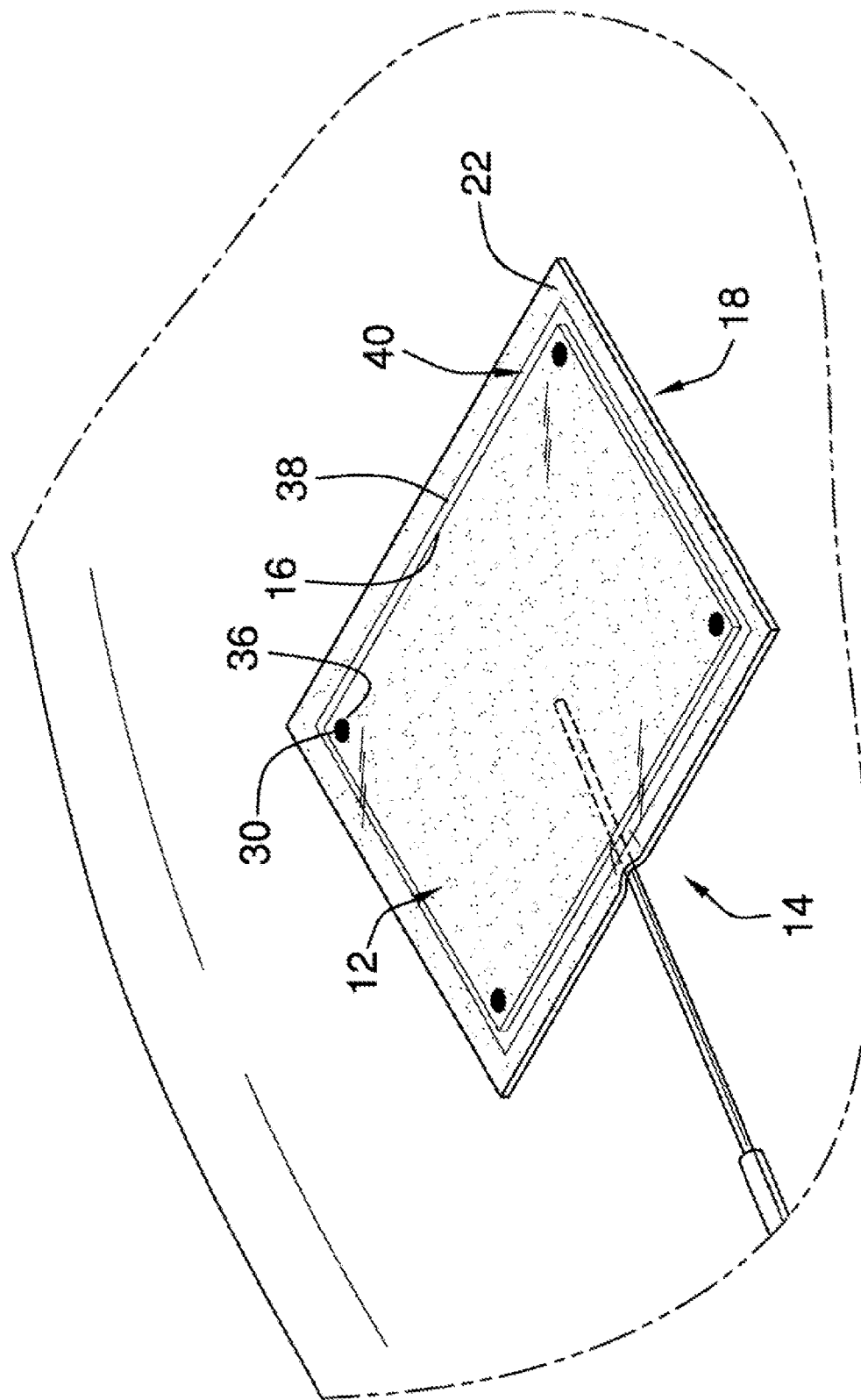
FIG. 3 is a top front side perspective view a site covering system, according to an exemplary embodiment of the present disclosure.
Figure 4:
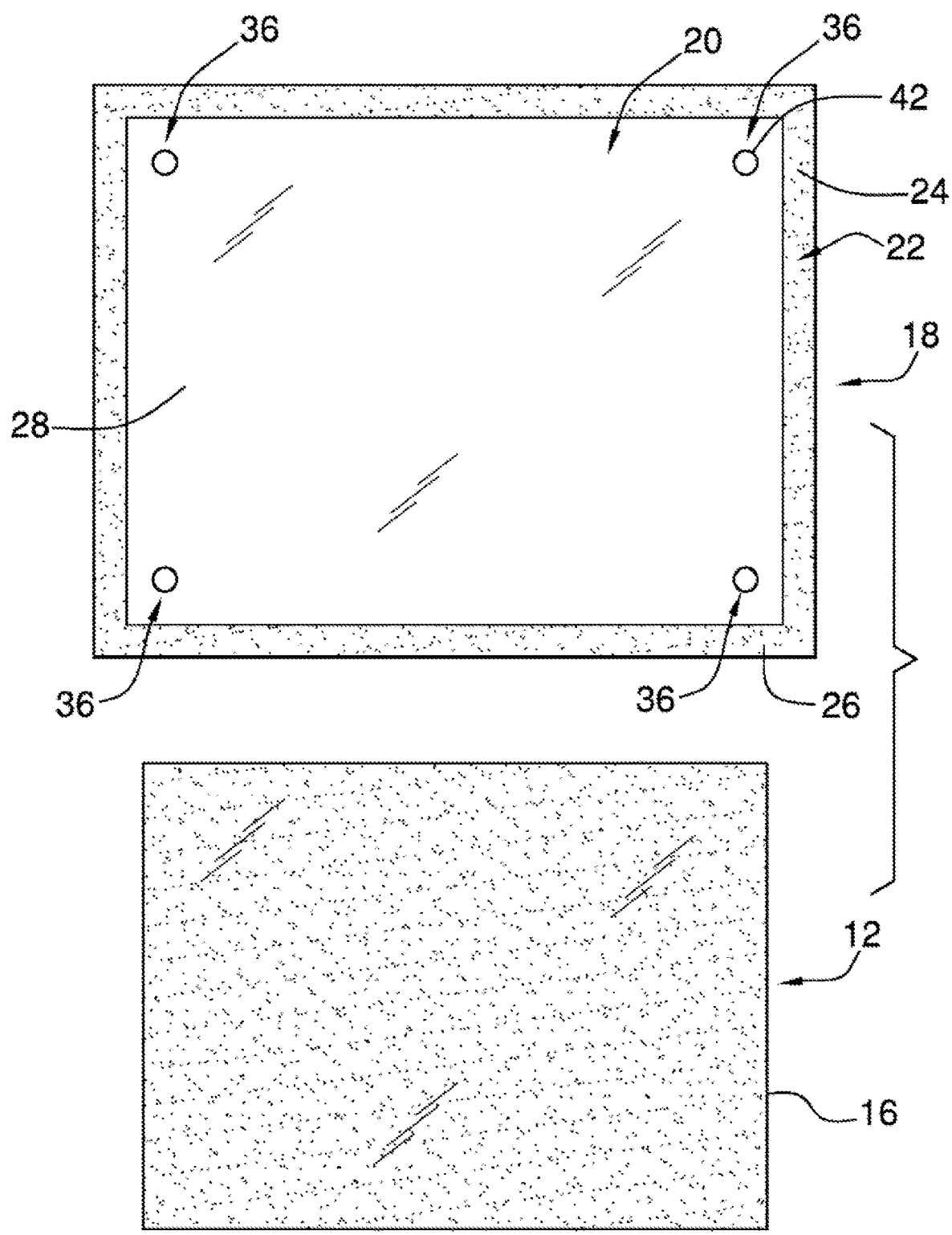
FIG. 4 is a bottom view of an embodiment of a site covering system, according to an exemplary embodiment of the present disclosure.
Figure 5:
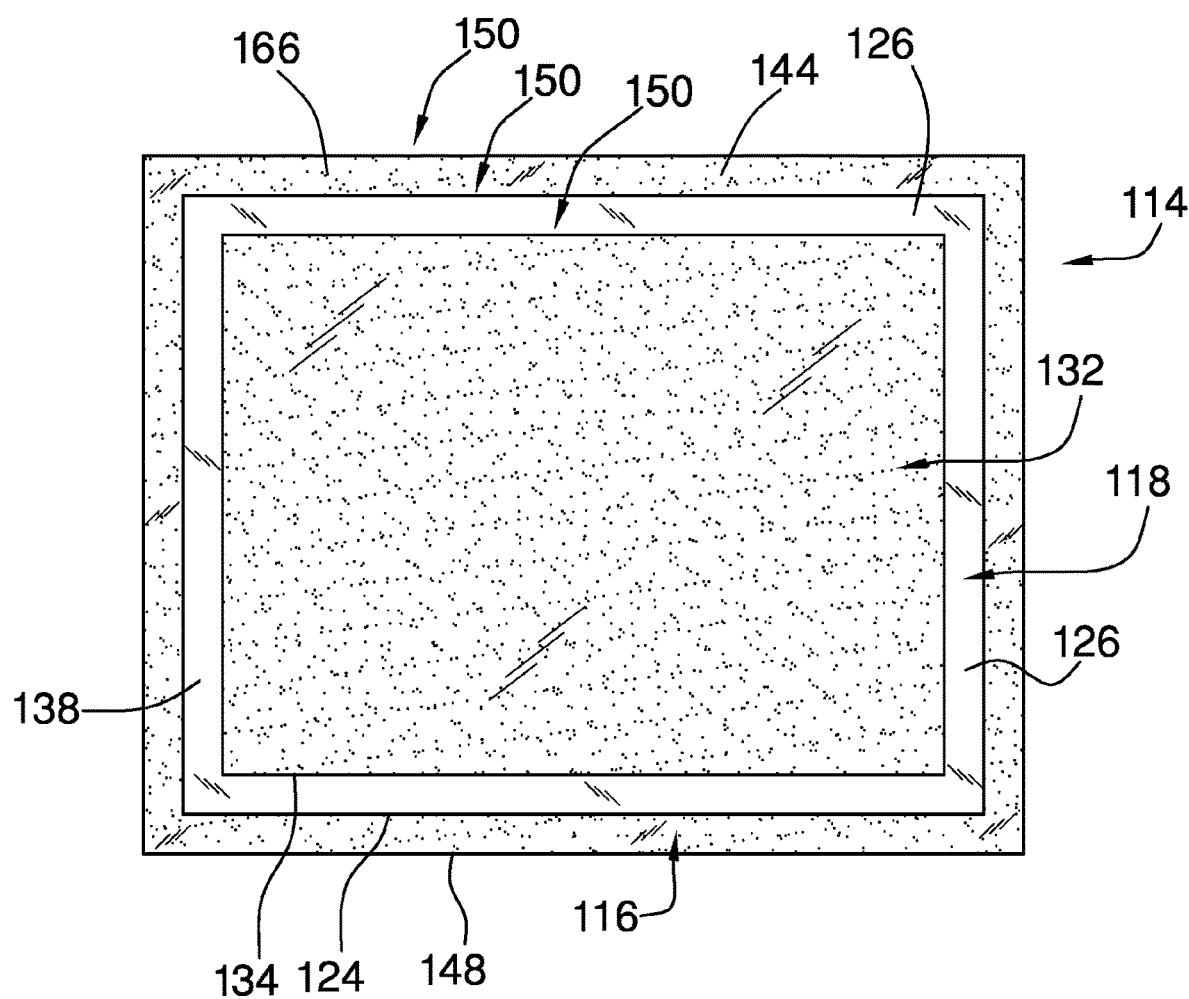
FIG. 5 shows a bottom view of a medical dressing system, according to an exemplary embodiment of the present disclosure.
Figure 6:
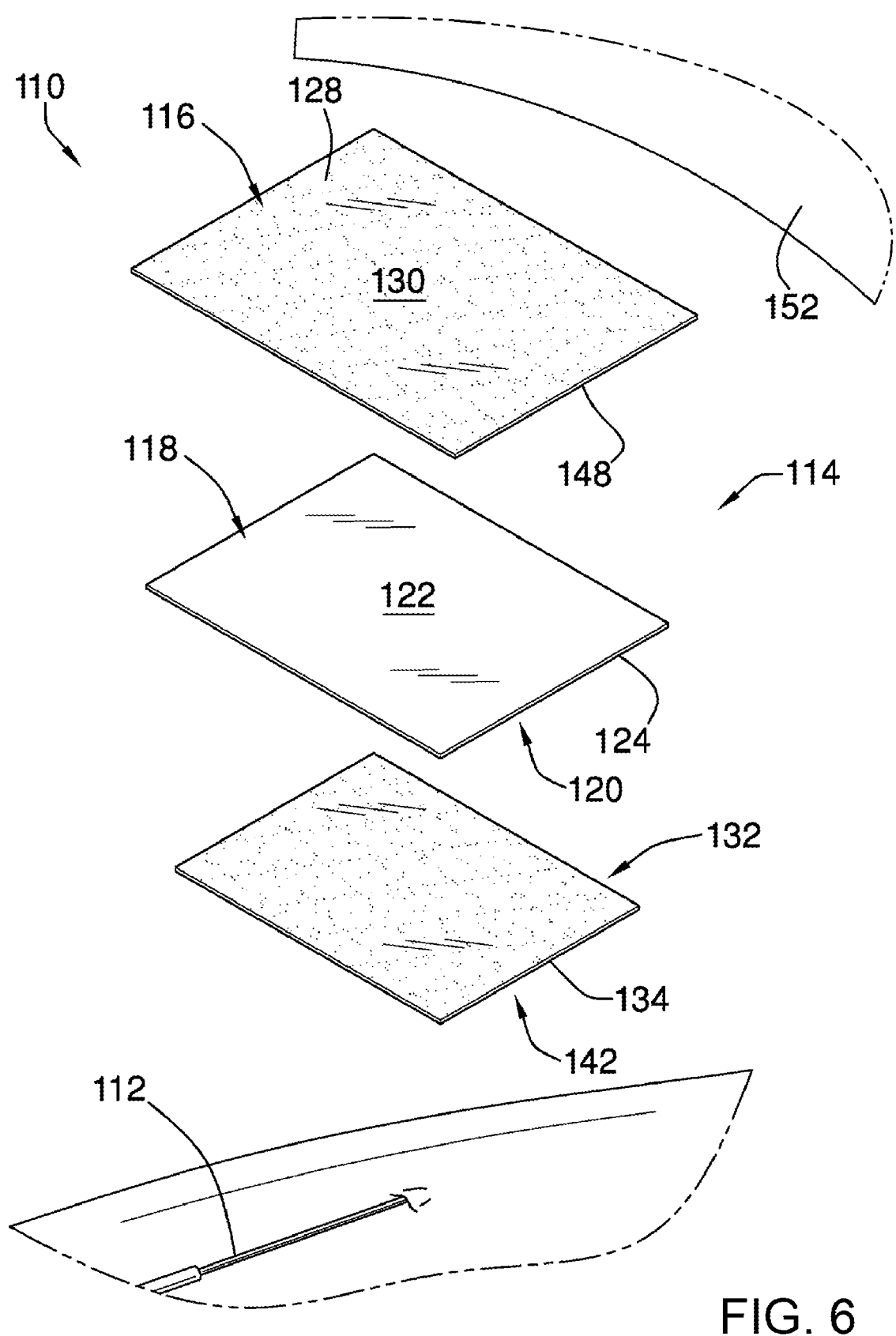
FIG. 6 shows an exploded top front side perspective view of a system, according to an exemplary embodiment of the present disclosure.
Figure 7:
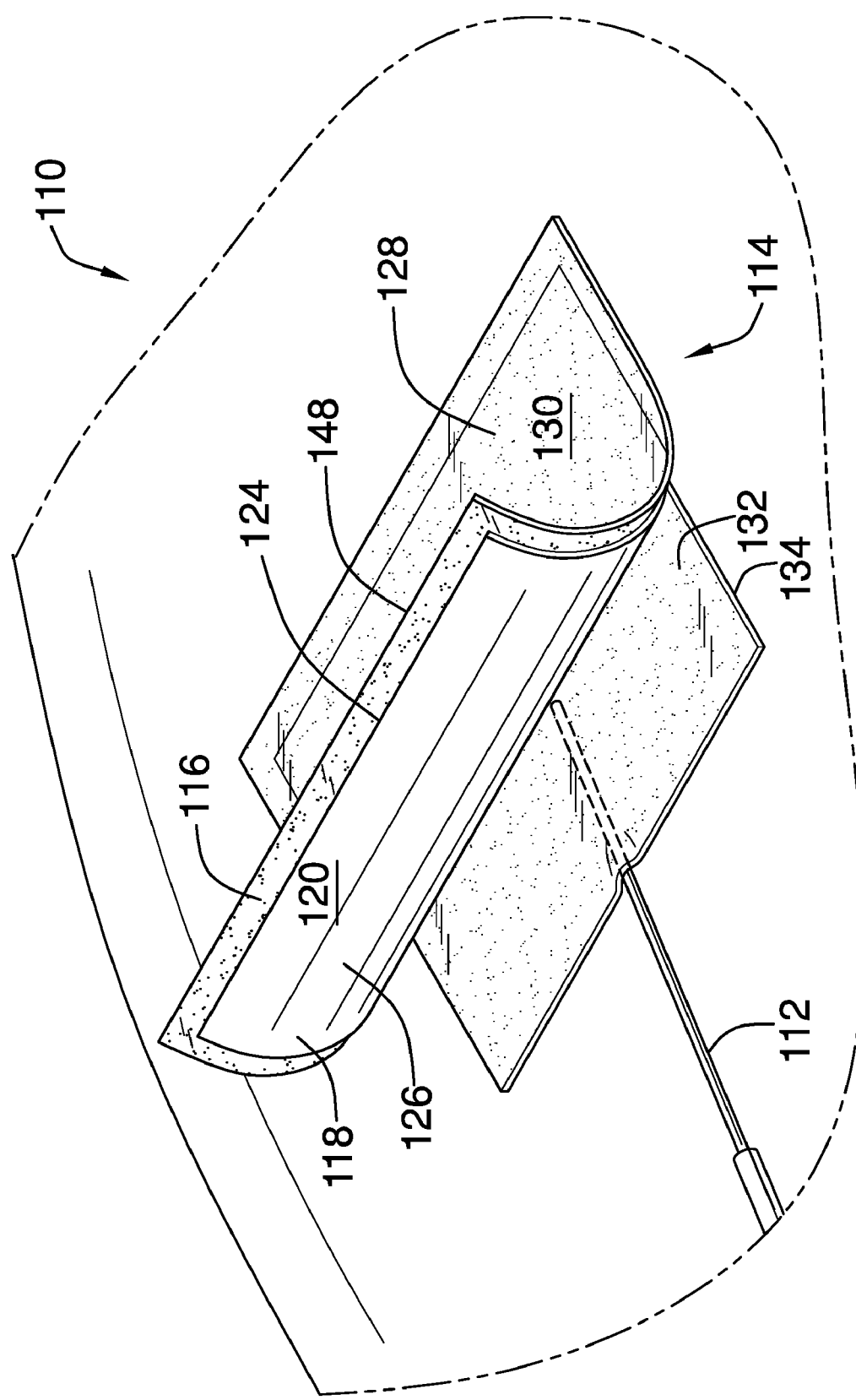
FIG. 7 shows a top front side perspective view of a system, according to an exemplary embodiment of the present disclosure.
Figure 8:
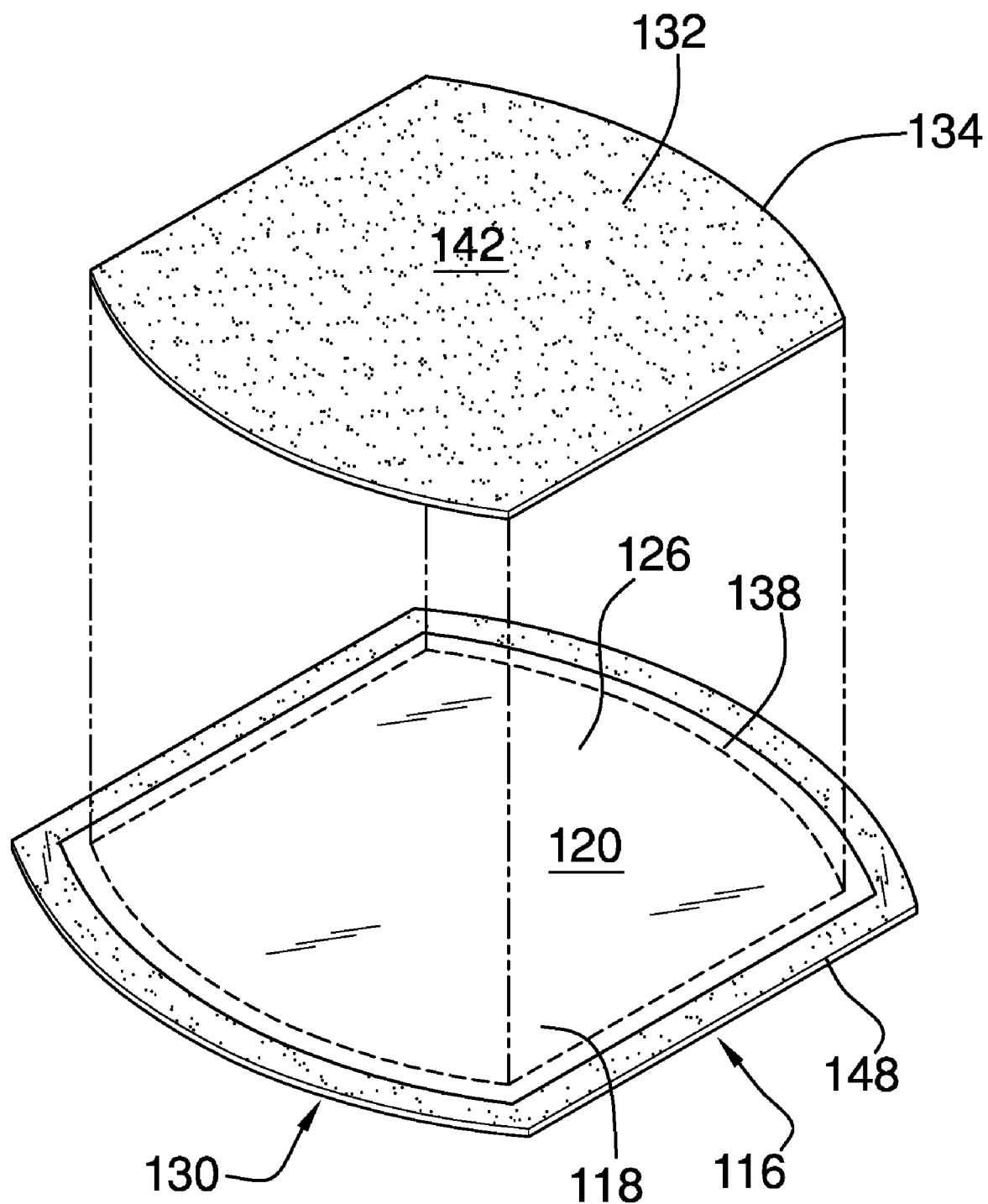
FIG. 8 shows a partially exploded bottom front side perspective view of a system, according to an exemplary embodiment of the present disclosure.

Primary dressings 12 of the present disclosure are configured to be adhered to the patient in a conventional manner when the surface of the primary dressing 12 to be adhered to the patient is fully (or at least partially, as disclosed further herein) covered by adhesive 24. The primary dressing 12 is configured to cover a medical site 14, such as shown in FIG. 2, thereby inhibiting the medical site 14 from being contaminated and inhibiting movement of the catheter relative to the patient. The primary dressing 12 embodiment, such as shown in FIGS. 9 and 11, has an outer perimeter edge 16. The outer perimeter edge 16 of the primary dressing 12 may be a geometric shape such as a square, rectangle, circle, oval, or the like.

A cover dressing 18, such as shown in FIGS. 9 and 10 for example, has a central section 20 and a peripheral section 22. The central section 20 of the cover dressing 18 is transparent wherein the primary dressing 12 is visible when viewed through the central section 20. The central section 20 has a shape and size substantially equivalent to the primary dressing 12. This provides for full coverage of the primary dressing 12 by the cover dressing 18 while minimizing bulk.

A cover adhesive 24 is positioned on a lower surface 26 of the peripheral section 22 wherein the lower surface 26 of the peripheral section 22 is configured for adhering to the patient around the outer perimeter edge 16 of the primary dressing 12. Thus, the central section 20 extends over and covers the primary dressing 12 such that the cover dressing 18 prevents contamination of the primary dressing 12. The cover adhesive 24 is positioned on the lower surface 26 of the peripheral section 22 extending completely around the central section 20 wherein the cover dressing 18 is fully occlusive of the primary dressing 12. A lower surface 28 of the central section 20 is free from adhesive wherein the cover dressing 18 is prevented from adhering directly to the primary dressing 12. Thus, the primary dressing 12 is configured to remain in place over the medical site 14 when the cover dressing 18 is removed from the patient. While specifically mentioned as applicable for the medical site 14, it is to be understood the primary dressing 12 may alternatively cover a wound or any other site on the patient where bandaging would be desired.

FIGS. 9 and 12 show an exemplary embodiment of a bottom sheet 80 of the present disclosure. As shown in FIG. 12, an exemplary bottom sheet 80 of the present disclosure comprises an outer portion 82 and an inner portion 84. Inner portion 84, as shown in FIG. 12, is configured to fit within outer portion 82 such that outer portion 82 contacts inner portion 84. Outer portion 82 and inner portion 84 are configured to detach from one another, such as by pulling tab 86.

As shown in FIG. 9, outer portion 82 of an exemplary bottom sheet 80 of the present disclosure is the primary feature that holds the cover dressing 18 and the primary dressing 12 together during application of the same to a patient. Procedurally, and in at least one exemplary method of the present disclosure, an exemplary covering system 10 of the present disclosure can be used by first removing inner portion 84 of bottom sheet 80, which would expose the majority of adhesive 24 present upon primary dressing 12. Outer portion 82 of bottom sheet would remain, which would be in adhesive contact with an outer perimeter portion of primary dressing 12 and with peripheral section 22 of cover dressing 18.

After inner portion 84 is removed, the remaining portions of covering system 10 can be applied to a location of interest of a patient. Once applied (adhered), tab 86 of outer portion 82 of bottom sheet 80 can be pulled, causing outer portion 82 to unravel or unwind from adhesive portions of primary dressing 12 and cover dressing 18, so that the entirety of adhesive portions of primary dressing 12 and cover dressing 18 are in contact with the patient.

Should it be desired to remove cover dressing 18, it can be removed by peeling it off the patient, noting that only peripheral section 22 (having adhesive 24 thereon) would be in adhesive contact with the patient. Removal of cover dressing 18 would have no effect on primary dressing 12, which would remain in contact with the patient. If desired, another cover dressing 18 can be applied on top of and around primary dressing 12, such that peripheral section 22 (having adhesive 24 thereon) would be in adhesive contact with the patient. This allows for a soiled, "old," or otherwise undesired cover portion 18 to removed and replaced, keeping the primary dressing 12 covered and protected from contamination.

Figure 13:
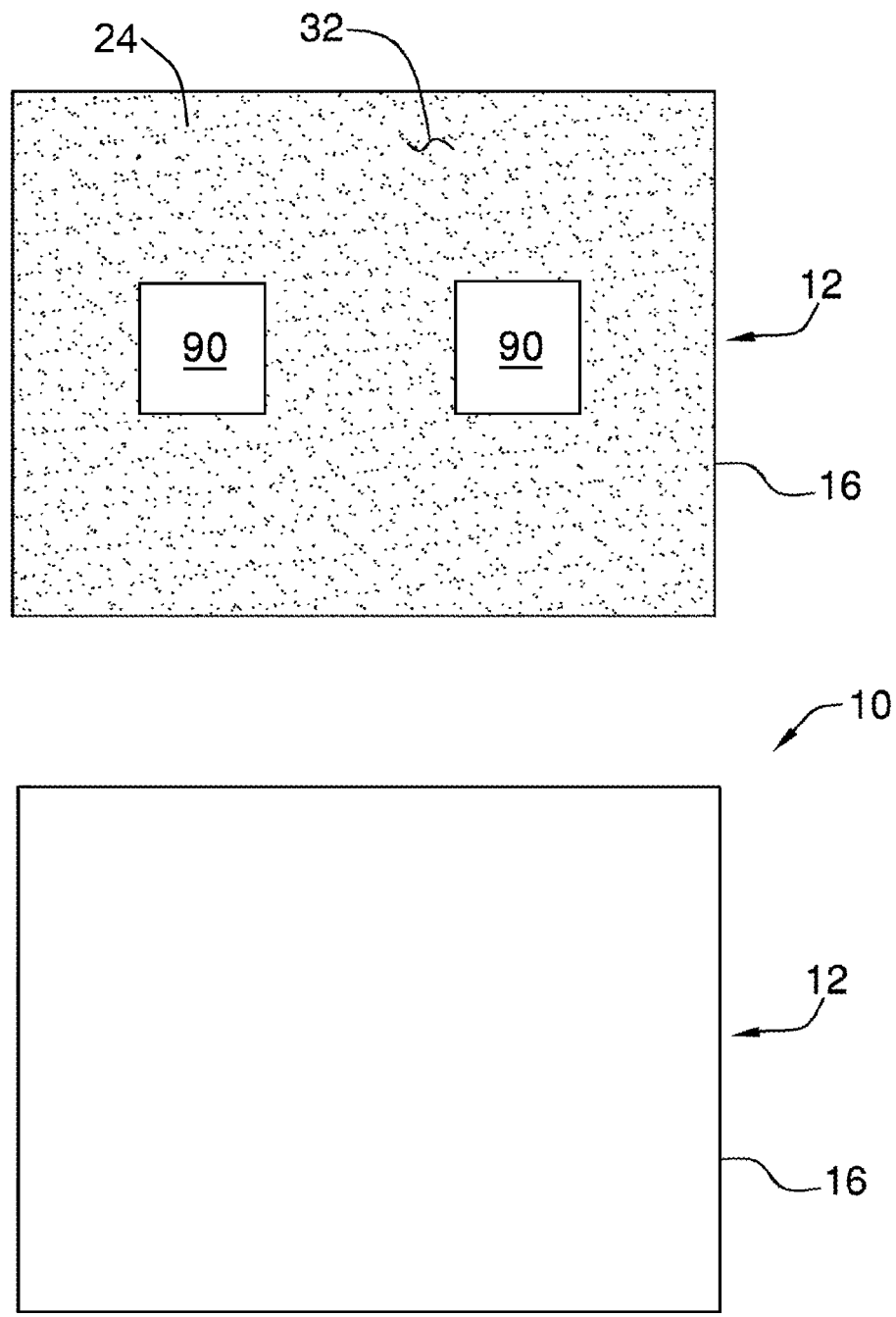
FIG. 13 shows a top view (upper portion of the figure) and a bottom view (lower portion of the figure) of a primary dressing of a medical dressing covering system, according to an exemplary embodiment of the present disclosure.
Figure 14:
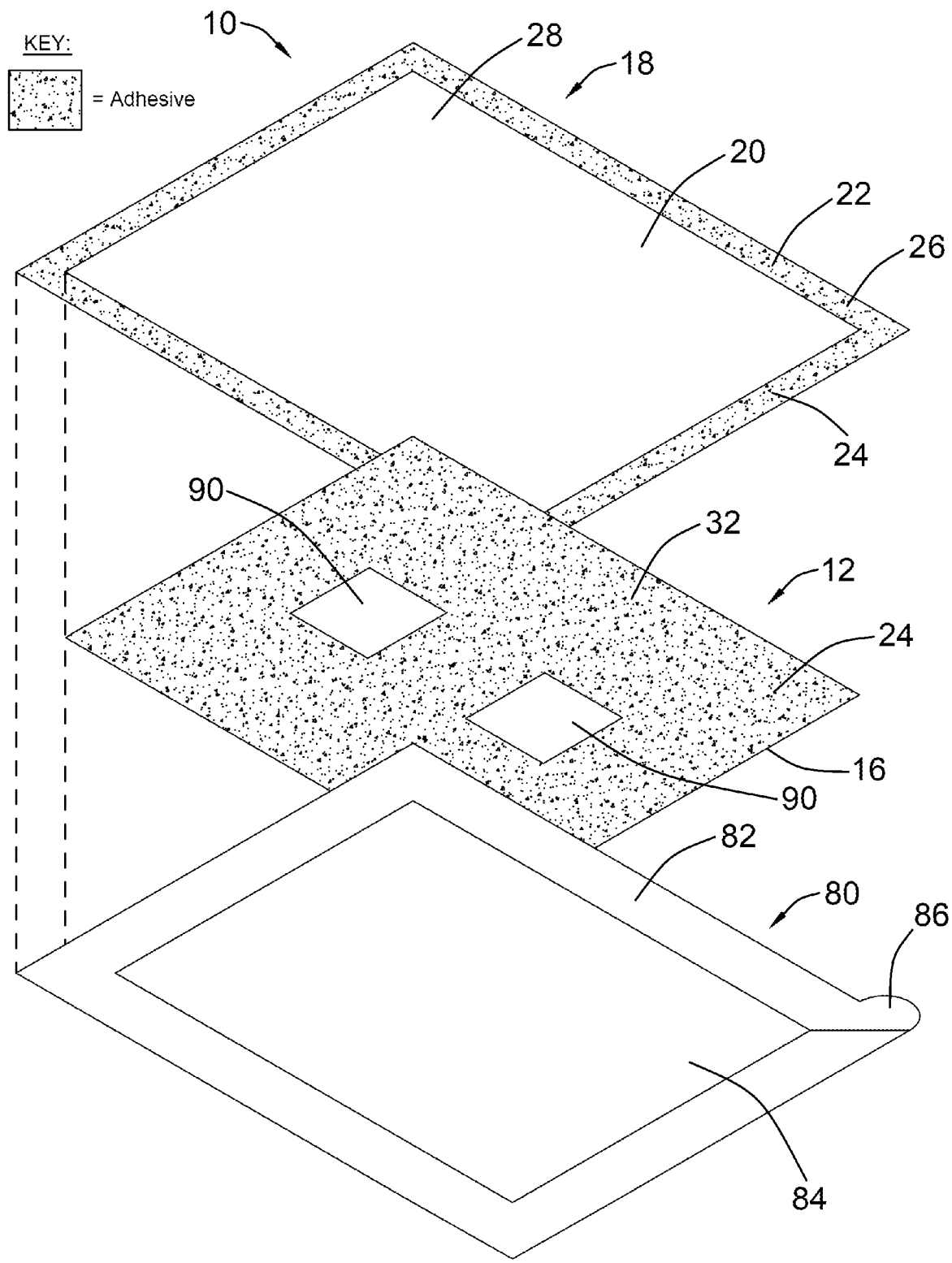
FIG. 14 shows a bottom view of a medical dressing covering system, according to an exemplary embodiment of the present disclosure.

An exemplary primary dressing 12 of the present disclosure can also have an internal section without adhesive 24. For example, and as shown in FIG. 13, an exemplary primary dressing 12 of the present disclosure can have one or more internal sections 90 defined therein that do not have any adhesive 24 applied thereto. This permits, for example, the use of a primary dressing 12 to cover a portion of the patient having a section that should not be covered by adhesive 24, such as an open wound, a stitched surface, a surface where skin needs to grow back, etc. Those locations can be covered by the one or more internal sections 90, while adhesive 24 from the remainder of the primary dressing 12 would contact the patient, keeping the locations of the patient covered by internal sections 90 free from contamination. FIG. 14 shows an exemplary system 10 of the present disclosure whereby primary dressing 12 has one or more internal sections 90 defined therein. Internal sections 90, in various embodiments, can comprise any number of non-adhesive materials, including, but not limited to, a non-adhesive material impregnated or coated with chlorhexidine gluconate and/or any number of other topical antiseptic products.

Figure 15:
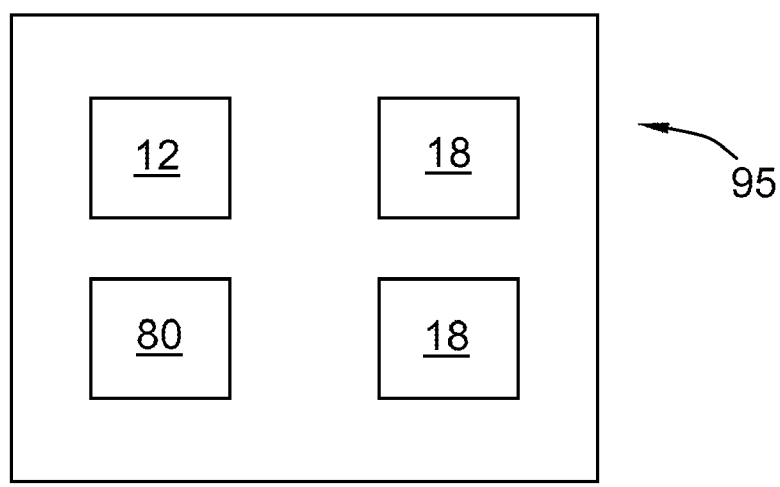
FIG. 15 shows a block diagram of components of a kit, according to an exemplary embodiment of the present disclosure.

The present disclosure also includes disclosure of a kit, such as shown in block diagram form in FIG. 15. As shown therein, an exemplary kit 95 of the present disclosure comprises at least a primary dressing 12 and two or more cover dressings 18. A bottom sheet 80 can also be part of an exemplary kit 95, such as when bottom sheet 80 covers an adhesive 24 positioned upon primary dressing.

In use, the cover dressing 18 is fully occlusive and protects the primary dressing 12. The cover dressing 18 can be removed if needed, such as by being contaminated by body fluids during a procedure. The cover dressing 18 is removed leaving the primary dressing 12 intact and uncontaminated. The base markings 30 on the primary dressing 12 facilitate proper positioning of the cover dressing 18. This allows for less bulk, easier application of the cover dressing 18, and helps to insure the gap 40 as desired to prevent the cover dressing 18 from adhesively engaging the primary dressing 12.

In various embodiments of systems 10 of the present disclosure, said systems 10 comprise two layers of product, such as a primary dressing 12 and a cover dressing 18, a dressing 114 and a base layer 132, and the like, whereby no third layer of product is required for use. Furthermore, it is noted that one or more features of exemplary primary dressings 12 and/or dressings 114 can be used and/or incorporated into other embodiments of primary dressings 12 and/or dressings 114. Similarly, one or more features of exemplary cover dressings 18 and/or base layers 132 can be used and/or incorporated into other embodiments of cover dressings 18 and/or base layers 132 of the present disclosure.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

The invention claimed is:

1. A dressing system, comprising:
    a primary dressing configured to adhere to a patient and to cover a location on the patient thereby inhibiting said location from being contaminated, said primary dressing defining an outer perimeter edge;
    a cover dressing having a central section and a peripheral section, said central section of said cover dressing being transparent wherein said primary dressing is visible when viewed through said central section;
    a cover adhesive positioned on a lower surface of said peripheral section upon the entire peripheral section wherein said lower surface of said peripheral section is configured to adhere to the patient around said outer perimeter edge of said primary dressing whereby said cover dressing extends over and covers said primary dressing such that said cover dressing prevents contamination of said primary dressing; and
    a bottom sheet configured to adhere to an adhesive portion of the primary dressing and the cover adhesive of the cover dressing;
    wherein the bottom sheet has an outer portion surrounding an inner portion, and wherein the inner portion is configured for removal from the bottom sheet independent of the outer portion.

2. The dressing system of claim 1, further comprising a tab defined upon the outer portion of the bottom sheet, whereby pulling said tab, after the inner portion has been removed and the dressing system applied to the patient, causes the outer portion to separate from the primary dressing and the cover dressing.

3. The dressing system of claim 1, wherein removal of the inner portion of the dressing system exposes adhesive present upon the primary dressing.

4. The dressing system of claim 1, wherein the primary dressing has an adhesive present upon an entirety of a side of the primary dressing.

5. The dressing system of claim 1, wherein the primary dressing has an adhesive present upon a portion of a side of the primary dressing.

6. The dressing system of claim 1, wherein the primary dressing has an adhesive present upon a side of the primary dressing with at least one internal section of the primary dressing being free of adhesive.

7. The dressing system of claim 6, wherein the at least one internal section of the primary dressing is coated or saturated with a topical antiseptic.

8. The dressing system of claim 1, wherein the primary dressing is sized and shaped to correspond to the size and shape of the central section of the cover dressing.

9. A method of using a dressing system, comprising:
    removing the inner portion of the bottom sheet of the dressing system of claim 1 to expose adhesive present upon the primary dressing; and
    positioning the remainder of the dressing system upon a patient at a desired location.

10. The method of claim 9, further comprising:
    pressing the cover dressing toward the patient to cause the adhesive on the primary dressing to adhere to the patient.

11. The method of claim 10, further comprising:
    removing the outer portion of the bottom sheet by pulling the tab; and
    pressing the cover dressing toward the patient again to cause the cover adhesive of the cover dressing to adhere to the patient.

12. The method of claim 11, further comprising:
    removing the cover dressing so that the primary dressing is fully exposed while being adhered to the patient.

13. The method of claim 12, further comprising:
    positioning a replacement cover dressing so that it surrounds the primary dressing adhered to the patient; and
    pressing the replacement cover dressing toward the patient to cause a cover adhesive of the replacement cover dressing to adhere to the patient, surrounding the primary dressing.

* * * * *